United States Patent
Makdissi

(10) Patent No.: US 8,359,096 B2
(45) Date of Patent: Jan. 22, 2013

(54) APPARATUS AND METHODS FOR AUTOMATIC OPTIMIZATION OF INTERVENTRICULAR AND ATRIO-VENTRICULAR DELAYS IN REAL TIME FOR CARDIAC RESYNCHRONIZATION IN AN ACTIVE IMPLANTABLE MEDICAL DEVICE

(75) Inventor: Alaa Makdissi, Paris (FR)

(73) Assignee: Sorin CRM S.A.S., Clamart (FR)

( * ) Notice: Subject to any disclaimer, the term of this patent is extended or adjusted under 35 U.S.C. 154(b) by 74 days.

(21) Appl. No.: 13/024,205

(22) Filed: Feb. 9, 2011

(65) Prior Publication Data

US 2011/0196443 A1 Aug. 11, 2011

(30) Foreign Application Priority Data

Feb. 9, 2010 (FR) ...................................... 10 50876

(51) Int. Cl.
*A61N 1/08* (2006.01)
(52) U.S. Cl. ................................ 607/17; 607/9; 607/15
(58) Field of Classification Search ................ 607/9, 15, 607/17
See application file for complete search history.

(56) References Cited

U.S. PATENT DOCUMENTS

| | | | |
|---|---|---|---|
| 5,304,208 A | 4/1994 | Inguaggiato et al. |
| 6,522,923 B1 | 2/2003 | Turcott |
| 6,556,866 B2 | 4/2003 | Dal Molin et al. |
| 6,604,002 B2 | 8/2003 | Molin |
| 6,725,091 B2 | 4/2004 | Dal Molin |
| 6,792,310 B1 | 9/2004 | Turcott et al. |
| 7,558,627 B1 | 7/2009 | Turcott |
| 7,613,507 B2 | 11/2009 | Vitali et al. |
| 2004/0078058 A1 | 4/2004 | Holmstrom et al. |
| 2005/0131469 A1 | 6/2005 | Cohen |
| 2007/0066905 A1 | 3/2007 | Zhang |
| 2008/0147130 A1 | 6/2008 | Rom |
| 2009/0105777 A1 | 4/2009 | Dong et al. |
| 2010/0121398 A1 | 5/2010 | Bjorling et al. |
| 2010/0145402 A1 | 6/2010 | Rom |

(Continued)

FOREIGN PATENT DOCUMENTS

| | | |
|---|---|---|
| EP | 0515319 | 12/1992 |
| EP | 1108446 | 4/2003 |

(Continued)

OTHER PUBLICATIONS

FR, Foreign Search Report (Annexe Au Rapport De Recherche Preliminaire Relatif A La Demande De Brevet Francais No. FR1050876 FA732832), Jul. 7, 2010.

(Continued)

*Primary Examiner* — Joseph Dietrich
(74) *Attorney, Agent, or Firm* — Orrick, Herrington & Sutcliffe, LLP

(57) ABSTRACT

An active implantable medical device for cardiac resynchronization with automatic and almost in real time optimization of the interventricular and atrio-ventricular delays is disclosed. The active implantable medical device includes a closed-loop for continuously controlling the atrio-ventricular delay AVD and the inter-ventricular delay VVD according to a hemodynamic signal delivered by a hemodynamic sensor. The closed-loop provides controlled modulation (38) and demodulation (42) the AVD, and modulation (48) and demodulation (52) the VVD, the modulation and demodulation being functionally interdependent (54, 56) by a sequence of alternating operation. A closed-loop regulator (36) for controlling the AVD receives as input an error signal ($E_{AVD}$) delivered based on demodulating the AVD (42) and outputs an AVD signal. A closed-loop regulator (46) for controlling the VVD receives as input a signal error ($E_{VVD}$) based on demodulating the DVV and outputs a VVD signal. In one embodiment, the regulators are PID controllers.

3 Claims, 6 Drawing Sheets

U.S. PATENT DOCUMENTS

2010/0185250 A1  7/2010  Rom

FOREIGN PATENT DOCUMENTS

| EP | 1116497 | 8/2003 |
| EP | 1138346 | 4/2004 |
| EP | 1741387 | 11/2009 |
| WO | WO 2006090397 | 8/2006 |
| WO | WO 2006126185 | 11/2006 |
| WO | WO 2008010220 | 1/2008 |
| WO | WO 2008133552 | 11/2008 |

OTHER PUBLICATIONS

David Tamborero et al., Optimization of the Delay in Cardiac Resynchronization interventricular Therapy Using the QRS Width, American Journal of Cardiology, Nov. 15, 2009, vol. 104, Issue 10, pp. 1407-1412.

JM Dupuis, et al.: Programming Optimal Atrioventricular Delay in Dual Chamber Pacing Using Peak Endocardial Acceleration: Comparison with a Standard Echocardiographic Procedure, PACE 2003; 26: [Pt II], 210-213.

APPARATUS AND METHODS FOR AUTOMATIC OPTIMIZATION OF INTERVENTRICULAR AND ATRIO-VENTRICULAR DELAYS IN REAL TIME FOR CARDIAC RESYNCHRONIZATION IN AN ACTIVE IMPLANTABLE MEDICAL DEVICE

The present application claims the benefit of French Application No. 10-50876 entitled "Active Implantable Medical Device for Cardiac Resynchronization with Automatic and Real Time Optimization of the Interventricular and Atrio-Ventricular Delays" and filed Feb. 9, 2010, which is hereby incorporated by reference in its entirety.

FIELD

The present invention relates to "active implantable medical devices" as defined by the 20 Jun. 1990 Directive 90/385/EEC of the Council of the European Communities, and more particularly to devices that continuously monitor a patient's heart rhythm and if necessary deliver to the heart of a patient electrical pulses for joint and permanent stimulation of the left and the right ventricles, so as to resynchronize them, said technique being known Cardiac Resynchronization Therapy as ("CRT") or Bi-Ventricular Pacing ("BVP").

BACKGROUND

Pacemakers providing CRT to a patient are known. One such device is disclosed, for example, in published European Application Publication No. EP 1108446 A1, filed Dec. 12, 2000, published Jun. 20, 2001, entitled "Implantable Active Device of Type Multisite Having Means for Resynchronization of Ventricles," and its counterpart U.S. Pat. No. 6,556,866 (assigned to Sorin CRM, previously known as ELA Medical), which is incorporated herein by reference and describes a device applying, between the respective instants of stimulation to the left and the right ventricles, a delay known as a variable interventricular delay (VVD). The VVD is adjusted so as to resynchronize the contraction of both left and right ventricles with fine optimization and improve the hemodynamic status of the patient.

A simultaneous stimulation of both left and right ventricles is not always optimal because it does not necessarily lead to a synchronous contraction of the ventricles. The delays of conduction in the left and right ventricular myocardium are not the same and may depend on multiple factors such as the location of the ventricular leads and the type of the ventricular leads (e.g., an over-the-wire lead implanted into the coronary sinus or an epicardial lead). It is therefore desirable to establish a delay between the two stimuli (i.e., VVD) and to adjust the delay VVD to resynchronize the contractions of the ventricles ensuring a fine optimization of hemodynamic parameters. Depending on the patient's clinical status, the VVD may be set to zero, positive (the left ventricle is stimulated after the right ventricle) or negative (the right ventricle is stimulated after the left ventricle).

A typical CRT pacemaker device runs a classic "dual chamber" operating mode in which the device monitors the ventricular activity after an atrial event that is either spontaneous (P wave detection of an atrial depolarization) or stimulated (application of an A pulse of atrial pacing). After detecting an atrial event, the device starts to count a delay period called "atrio-ventricular delay" (AVD) such that if no spontaneous ventricular activity (R wave detection of a ventricular depolarization) is detected after this AVD, then the device triggers a stimulation of the ventricle (application of a V pulse of ventricular pacing).

Clinical studies have demonstrated often dramatic improvements for patients with congestive heart failure ("CHF") whose condition was not improved by conventional CHF therapies by precisely adjusting the parameters of the CRT therapy according to the patient's clinical condition and to the nature of specific myocardial contraction disorders such as dilated heart chambers, low ejection fraction, and excessive lengthening of the duration for the QRS complex (whether this disorder is spontaneous or induced by a traditional stimulation).

It is also necessary to reassess these parameter settings to optionally re-adjust them if necessary: indeed, the benefits provided by the CRT therapy may eventually lead to modifying the original configuration and the parameter settings.

The standard technique for adjusting CRT stimulation parameters starts with the estimation of the characteristic delays of the systole by echocardiography, especially the timing of opening of the aortic valve. However, this procedure should be implemented in hospitals and by qualified personnel. This procedure is long and costly, thus cannot be applied as often as it would be useful or necessary without interfering with the patient's daily life, despite the beneficial effects on the CRT therapy.

Another inherent difficulty with the echocardiographic assessment is that it requires testing several successive pacing configurations, and determining an optimal AVD for each pacing configuration. Therefore, the number of combinations to be tested is important, and involves a complicated and time consuming procedure that is difficult to manage excluding it from a routine operation.

Therefore, there is a need for a technique for evaluating in a simple, rapid, automated and precise procedure the impact of different CRT stimulation parameters, including the AVD and VVD delays, so as to optimize the patient's hemodynamic status.

One automated method of optimization is described in the article by J M Dupuis, et al.: *Programming Optimal Atrio-ventricular Delay in Dual Chamber Pacing Using Peak Endocardial Acceleration: Comparison with a Standard Echocardiographic Procedure*, PACE 2003; 26: [Pt II], 210-213. This technique involves, while scanning the AVD in a given stimulation setup to trace a characteristic, generating a value of the peak of endocardial acceleration ("PEA") according to the AVD. The considered optimal value of the AVD is the inflection point of the characteristics, i.e., the point corresponding to a maximum duration of ventricular filling without truncating the A wave (i.e., a minimum delay between the closing of the mitral valve and the beginning of the QRS complex).

Even if the corresponding algorithm gives satisfactory results, it takes up to several minutes before an optimal pair {AVD, VVD} is selected because multiple scans of AVD are required for various values of VVD that are separately tested.

Another drawback of this optimization technique is that the search for each delay period (AVD or VVD) is independent of the other: for a given VVD, a scan of the AVD gives a locally optimal AVD, but (as is explained in greater detail below with particular reference to FIG. 5) the convergence to a local optimum does not necessarily lead to the global optimum. In other words, the optimal pair {AVD, VVD} does not necessarily correspond to an optimal AVD value, at constant VVD, or to an optimal VVD value, at constant AVD.

A special technique of optimization, which is faster, thus implementable in real time, is described in WO 2006/090397

A2 and WO 2006/126185 A2. The algorithm described in these documents use a spike neural network to identify the maximum of a hemodynamic function (stroke volume). A spike network, however, requires a dedicated processor, thus involving the design of a specific, more complex device demanding higher power consumption. A software implementation of this algorithm is possible, but in such a case, it requires computing resources that are unattainable in ultra-low power consumption microcontrollers adequate for use in implantable medical devices.

WO 2008/010220 describes yet another technique, in which a spike neural processor is combined with a reinforced learning algorithm (Q-learning), which learns and associates the cardiac conditions to the optimal delays. Using this Q-learning can offer improved immunity to noise and increase the speed of convergence of the control algorithm. However, in order to achieve this performance, additional hardware resources are required including a microprocessor in addition to the spike neural processor, which incurs extra cost, higher power consumption, and increased spatial requirements for an implant device.

OBJECT AND SUMMARY

It is, therefore, an object of the present invention to provide a new, simple, rapid, automated and efficient technique for simultaneously optimizing both AVD and VVD parameters, despite the interdependent nature of these two parameters.

It is further an object of the present invention to apply the optimization technique almost in real time, preferably with a response time of only a few cardiac cycles, and implementing the optimization technique in simple material and software resources that are available in a current implantable device such as a CRT pacemaker.

According to one embodiment of the present invention, a parameter pair (couple) {AVD, VVD} is optimized exploiting a hemodynamic surface, i.e., a function of two variables $Z=f(AVD, VVD)$ rather than separately utilizing the two distinct characteristics (i.e., two distinct functions having each of the two variables such as $Z_1=f_1(AVD)$ and $Z_2=f_2(VVD)$). This hemodynamic surface represents the combinational characteristics of the entire system including the CRT device, the patient's heart, and the hemodynamic sensor, thus the characteristics varies with the current AVD and VVD values programmed into the CRT device, the patient's condition, and the type of hemodynamic sensor used.

In one embodiment of the present invention, a digital closed-loop system having a conventional proportional-integral-derivative (PID) digital controller is used for monitoring or tracking an optimal point on the hemodynamic surface. The implementation of the digital closed-loop system in the CRT device requires only incremental material and/or software resources without incurring extra cost and design for an additional hardware.

The present invention is generally directed to an active medical device, such as an implantable device for cardiac resynchronization by biventricular pacing, comprising (i) means for detecting atrial and ventricular events; (ii) means for stimulating the right and left ventricles; (iii) a sensor delivering a signal representative of a patient's current hemodynamic parameter; (iv) means for delivering to the stimulation means an atrio-ventricular delay AVD, calculated from the moment of detection of a spontaneous or paced atrial event and after which a stimulation of the right ventricle is delivered in the absence of a detected spontaneous ventricular event; (v) means for delivering to the stimulation means an inter-ventricular delay VVD between respective times of stimulation of right and left ventricles, and (vi) a closed-loop controller, continuously monitoring the AVD and the VVD according to the hemodynamic signal delivered by the sensor.

In one embodiment of the present invention, the closed-loop controller responds to the signal delivered by said at least one sensor and generates an AVD error signal representative of a difference between the current value of the AVD and an optimal value of AVD; and a VVD error signal representative of a difference between the current value of the VVD and an optimum value of VVD. The closed-loop controller further includes an AVD closed-loop regulator, receiving as input said AVD error signal and delivering as output an AVD signal; and a DVV closed-loop regulator, receiving as input said VVD error signal and delivering as output a VVD signal.

In a preferred embodiment, the AVD and VVD closed-loop regulators are PID regulators.

Preferably, generating the AVD or VVD error signal is obtained by a controlled modulation and demodulation of the AVD or VVD, respectively.

In one embodiment, the closed-loop controller has (i) means for generating the AVD error signal according to the signal delivered by the at least one sensor, (ii) means for generating the VVD error signal according to the signal delivered by the at least one sensor, (iii) means for modulating and demodulating the AVD, and (iv) means for modulating and demodulating the VVD. The two means of generation of error signals for the AVD and the VVD, the respective means for modulating and demodulating the VVD and the AVD, are functionally interdependent. In this embodiment, it is particularly preferable to provide that the means for modulating and demodulating in a controlled manner the VVD and the AVD, as well as the regulators for controlling the AVD and the DVV, operate alternatively in the control of the AVD and the VVD respectively, for a predetermined number of cardiac cycles, such that the regulator for controlling the AVD is inoperative during the modulation/demodulation of the VVD, and vice versa.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION OF THE INVENTION

With reference to FIGS. 1-13, various embodiments of the present invention will now be described. As regards its software aspects, the present invention can be implemented by an appropriate programming of the controlling software of a known device, for example, a cardiac pacemaker or a defibrillator/cardioverter, including means for collecting signals provided by endocardial leads and/or one or more implanted sensors.

The present invention is directed to apparatus and method for implementing the functions of automatic and in almost real time optimization of the AVD and VVD. One such device includes programmable microcontroller and/or microprocessor circuitry to receive, format, process electrical signals collected (detected) by one or more implanted electrodes, and deliver stimulation pulses to these electrodes. It is possible to transmit by telemetry software and store it in a memory of the implantable device to execute the functions of the present invention that will be described herein. The adaptation of these devices to implement the functions and features of the present invention is believed to be within the abilities of a person of ordinary skill in the art, and therefore will not be described in detail. One suitable device to which the present invention may particularly be applied are those of the Paradym CRT device family, produced and marketed by Sorin CRM, Clamart France, formerly known as ELA Medical, Montrouge, France.

Figure 1:
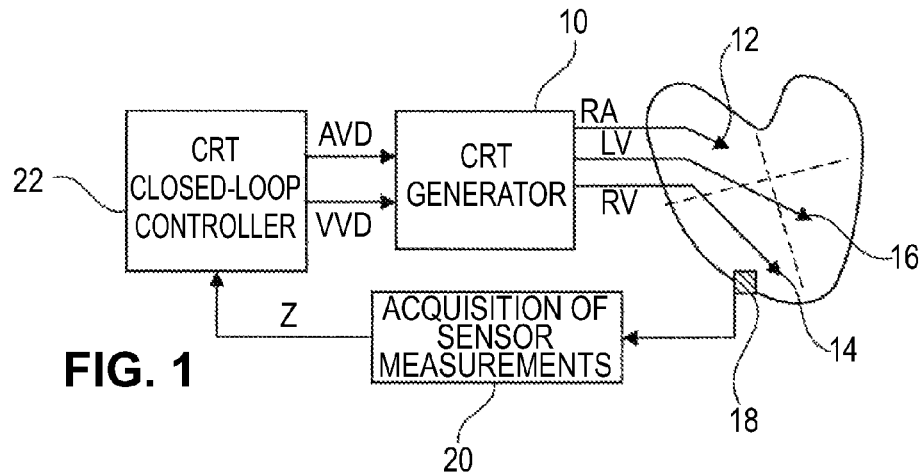
FIG. 1 is a block diagram of a system for the closed-loop, real-time hemodynamic CRT device, according to one embodiment.

The various elements involved in the present technique of closed-loop real-time hemodynamic optimization of the AVD and VVD parameters in accordance with the invention are illustrated in a schematic functional block in FIG. 1. The reference 10 denotes the generator of the CRT device connected to the heart via leads to collect depolarization signals of the myocardium and stimulate the myocardium by delivering electrical pulses to the different cavities of the heart. A lead 12 implanted in the right atrium (RA), and a lead 14 implanted in the right ventricle (RV) allows optimizing the atrio-ventricular delay AVD between the instants of stimulation of the right atrium and the right ventricle. A lead 16 implanted inside or in the vicinity of the left ventricle (LV), in combination with the lead 14 implanted in the right ventricle, allows optimizing the interventricular delay VVD between the left and right ventricles.

A hemodynamic sensor 18 measures hemodynamic signals representing cardiac output from the heart. More specifically, the hemodynamic sensor 18 estimates the changes in contractility, correlated with increases in blood pressure. Hemodynamic sensors differ from activity sensors (for example, acceleration sensors) or metabolic sensors (for example, minute ventilation sensors) that are intended to diagnose the presence or level of an activity by the patient and to quantify the patient's metabolic needs. Depending on the patient's level of activity or metabolic needs, the stimulation heart rate is adapted. However, the hemodynamic sensor 18 not only monitors the patient's efforts, similarly to metabolic or activity sensors, but also gives an indication of the patient's hemodynamic tolerance in certain events, especially the tolerance to a change in the AVD and VVD parameters by the device.

In a preferred embodiment, the hemodynamic sensor 18 is an intracardiac pressure sensor that measures the pressure difference $\Delta_{pp}$ between the systolic and the diastolic pressures, or an endocardial acceleration sensor that is capable of detecting Peak Endocardial Acceleration (PEA) signals.

These examples of hemodynamic sensors are, however, in no way limitative, and the present invention may be implemented with other types of hemodynamic sensors such as: an epicardial acceleration sensor (not endocardial), a cardiac wall motion sensor, an intracardiac bioimpedance sensor, an optical oxygen saturation sensor, and an ultrasound sensor for measuring changes in blood volume.

It should be understood that the hemodynamic signals used in the analysis for the optimization of the AVD and VVD may be obtained from an external sensor instead of an implanted sensor, for example, through an accelerometer sensor attached to the patient's chest at the sternum.

For various descriptions of hemodynamic sensors, reference may be particularly made to the following documents, which are incorporated herein by reference:

an endocardial acceleration sensor of the PEA type: Published European Application Publication No. EP 0515319 A1, filed May 12, 1992, published Nov. 25, 1992, entitled "A Cardiostimulator Device of the Rate-Responsive Type," and its counterpart U.S. Pat. No. 5,304,208, assigned to Sorin Biomedica Cardio SpA describe a method to collect endocardial acceleration signals using a lead provided with a distal endocardial stimulation electrode implanted at the apex of the ventricle and measuring the endocardial acceleration using a micro-accelerometer. Published European Application Publication No. EP 0655260 A1, filed Oct. 5, 1994, published May 31, 1995, entitled "Device for Determining Myocardial Function and Corresponding Procedure," and its counterpart U.S. Pat. No. 5,693,075, also assigned to Sorin Biomedica Cardio SpA describe a method to treat the measured endocardial acceleration signals to notably derive endocardial acceleration peak values corresponding to the two major noises that are identifiable in each heart cycle of a healthy heart;

a transvalvular bioimpedance sensor measured between the atrium and the ventricle located on the same side of the heart: Published European Application Publication No. EP 1116497 A1, filed Jan. 12, 2001, published Jul. 18, 2001, entitled "Active Implantable Medical Device, In Particular Pacemarker, Defibrillator and/or Multisite Device Having Means to Measure Transvalvular Impedance," and its counterpart U.S. Pat. No. 6,604,002 assigned to Sorin CRM S.A.S previously known as ELA Medical describe a dynamic measurement of bioimpedance (BioZ) to assess the diastolic and systolic volumes and obtain an indication of the cardiac output and thus, an indication of the ejection fraction;

a transseptal bioimpedance sensor measured between a site located on one side of the heart and a site located on the other side: Published European Application Publication No. EP 1138346 A1, filed Mar. 14, 2001, published Oct. 4, 2001, entitled "Active Implantable Medical Device Having Means For Measuring Transseptal Bioimpedance," and its counterpart U.S. Pat. No. 6,725,091 assigned to Sorin CRM S.A.S previously known as ELA Medical describe another type of measure useful to deliver a representative value of the ejection fraction; and an external accelerometer sensor: Published European Application Publication No. EP 1741387 A1, filed Jun. 21, 2006, published Jan. 10, 2007, entitled "Device for Non Invasive Detection of Occurrence of Sleep Apnea or Hypopnea," and its counterpart U.S. Pat. No. 7,613,507 assigned to Sorin CRM S.A.S previously known as ELA Medical describe the method to collect endocardial acceleration signals using a lead placed on the patient's chest.

Whether the hemodynamic sensor is implanted (transvenous, epicardial . . . ) or externally placed, it delivers signals correlated with the cardiac output and transmits the signals to an acquisition circuit 20. Acquisition circuit 20 preferably is incorporated in the generator 10 of the device, or but alternatively, it may be separately packaged from the generator 10 and located outside the patient's body.

The acquisition circuit 20 delivers a signal Z, hereinafter referred to as a "signal" or a "hemodynamic signal", to a closed-loop controller 22 and more preferably a PID controller. The transmission from the acquisition circuit 20 to the controller 22 can be direct (in the case of a treatment which is purely internal to the implant), or by telemetry (in the case of an external sensor and a controller 22 incorporated into the implant, or in the case of an implanted sensor and of an external controller 22 that is integrated into a programmer used for setting up the generator during a visit to a practitioner).

The controller 22 implements a closed-loop algorithm to concurrently obtain optimal values of the AVD and of the VVD.

It should be understood that it is possible to use multiple sensors for controlling a delay (e.g., an accelerometer and a bioimpedance sensor for controlling the AVD), or to use a different sensor for each delay (e.g., a bioimpedance sensor to control the VVD and a PEA sensor to control the AVD or vice versa). In any event, whatever the type or number of sensors used, the acquisition circuit 20 delivers a piece of information Z as a function of two variables Z=f (AVD, VVD). The function Z can be graphically represented by a surface and hereinafter referred to as a "hemodynamic surface".

Figure 2:
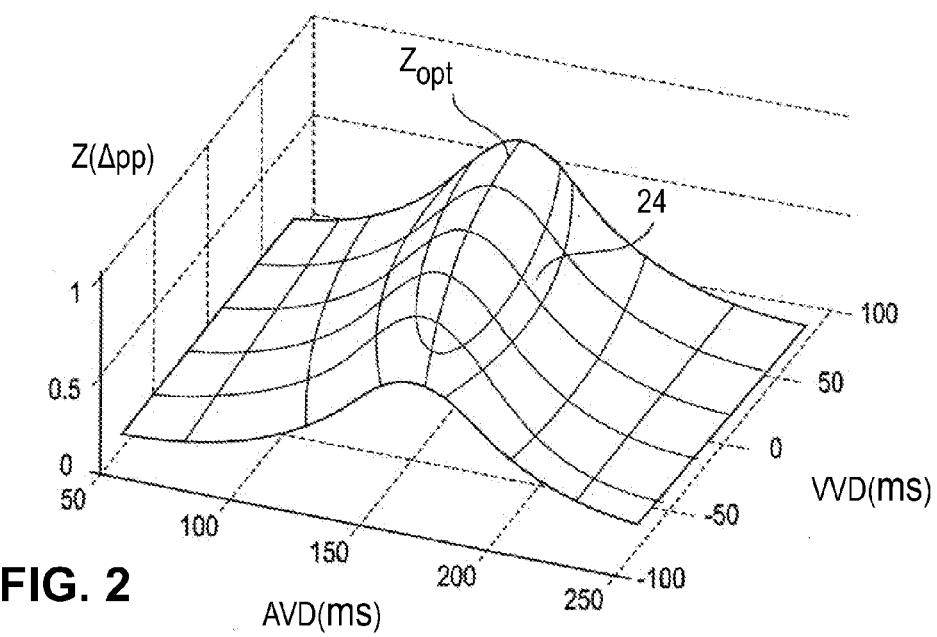
FIG. 2 is a representation of a hemodynamic surface, in the case of a sensor measuring the differences between the systolic and the diastolic pressures.

FIG. 2 illustrates an example of a hemodynamic surface Z=f (AVD, VVD). In this case, the hemodynamic sensor 18 is blood pressure sensor delivering signals to obtain a piece of information Z representative of a difference $\Delta_{pp}$ between the systolic pressure and the diastolic pressure. The optimum of a hemodynamic surface 24 is located at the point $Z_{opt}$ having the highest Z score. In practice, the vicinity of this optimum $Z_{opt}$ in the hemodynamic surface 24 may be approximated by parabolic characteristics in the plane {VVD, Z} and in the plane {AVD, Z}.

Figure 3:
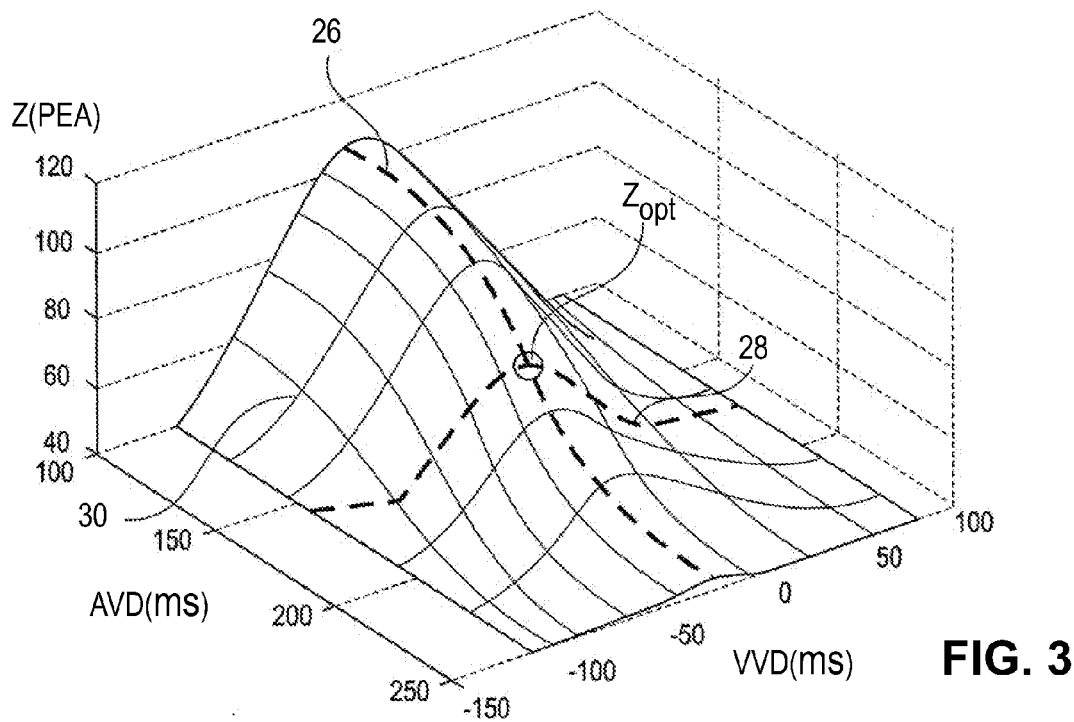
FIG. 3 is a representation of a hemodynamic surface, in the case of a sensor measuring the value of the peak of endocardial acceleration (PEA)

FIG. 3 illustrates another example of hemodynamic surface Z=f (AVD, VVD). In this case, the hemodynamic sensor 18 is an endocardial acceleration sensor delivering signals to obtain a piece of information Z representative of the peak of endocardial acceleration PEA. More specifically, the first peak of endocardial acceleration ("PEA1") corresponds to the closure of the mitral and tricuspid valves, at the beginning of the phase of isovolumetric ventricular contraction (systole), and its variations are closely linked to the variations of blood pressure in the ventricle representing the myocardial contractility. The amplitude of the PEA1 peak is particularly correlated to the positive maximum of the pressure variation dP/dt in the left ventricle.

The signal variations as a function of AVD follow a relation Z=f (AVD), represented by a characteristic curve 26 in the form of a sigmoid, while the variations of the same signal as a function of VVD follow a relation Z=f (VVD) represented by an approximately parabolic characteristic curve 28. In this case, the optimal value of the couple {AVD, VVD} corresponds to the intersection point $Z_{opt}$ between the inflection point of the sigmoid characteristic curve 26 and the highest point of the parabolic characteristic curve 28.

Figure 4:
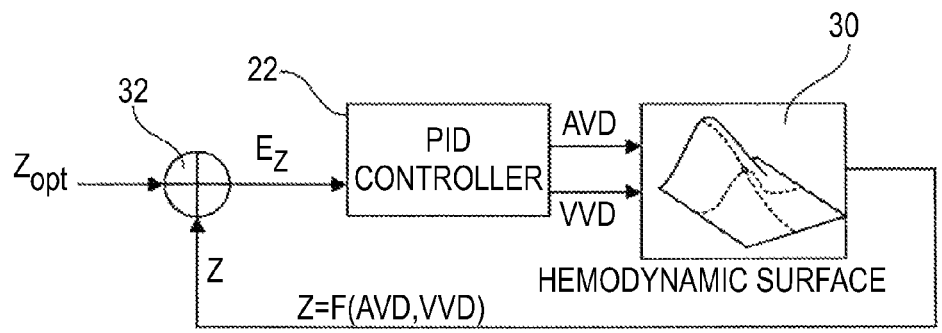
FIG. 4 illustrates a PID loop controller applied to a closed-loop hemodynamic of a CRT device.

FIG. 4 illustrates an exemplary functional diagram of a closed-loop of the system of FIG. 1. A controller 22 outputs the two values AVD and VVD, from an input $E_Z$ representing the error between the current value Z=f (AVD, VVD) obtained from the value measured by the hemodynamic sensor 18 and a reference value corresponding to the desired optimum $Z_{opt}$ of the hemodynamic surface 30. The hemodynamic surface 30 characterizes the response Z=f (AVD, VVD) of the group consisting of: the CRT resynchronization generator 10, the patient's heart, the hemodynamic sensor 18 and the acquisition circuit 20.

In one embodiment, the controller 22 is a digital PID controller for closed-loop control delivering any combination of the following output control signal components:

proportional component ("P"): the output is proportional to the error signal $E_Z$;

integral component ("I"): the output is the sum of the instantaneous error signal $E_Z$ over time. The output is increased as the error $E_Z$ accumulates over time, thus eliminating the residual stead-state error, and derivative component ("D"): the output is proportional to the time derivative of the error $E_Z$ creating an accelerated response in case the error rate ($dE_Z/dt$) increases.

In the case of a digital controller operating on discrete values, such a closed-loop system works intermittently in successive steps (each step in this case corresponding to a cardiac cycle). In this case, it is necessary to wait to the end of the cardiac cycle k to obtain the value $Z_k$ that represents the value of the hemodynamic function during the corresponding cardiac cycle.

A conventional PID controller may not be directly used to implement the present invention because:

the target point value $Z_{opt}$ is not known or not available a priori and a conventional PID controller has a single input and a single output (SISO), whereas in the present case it is necessary to simultaneously monitor two variables, namely the AVD and the VVD.

Nor is it possible to split the system so as to separately and simultaneously control the AVD and the VVD with two PID controllers because duplicate controllers do not ensure convergence to an optimal point.

Figure 5:
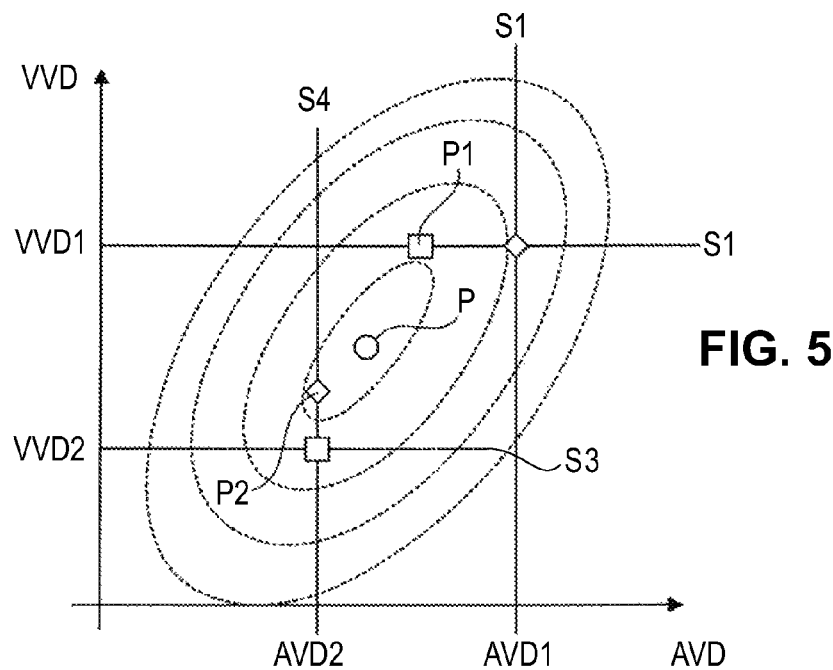
FIG. 5 illustrates the case of a separate optimization of the AVD and of the VVD independently, without interaction.

These drawbacks of using a conventional PID controller for the implementation of the present invention are more specifically explained with reference to FIG. 5. The hemodynamic surface of FIG. 5 corresponds to the parabolic surface as shown in FIG. 2 where the parameter Z is a function of the difference $\Delta_{pp}$ between the systolic pressure and the diastolic pressure. In a plane {AVD, VVD}, the contours correspond approximately to ellipses, shown in dotted lines with a global optimum $Z_{opt}$ at point P.

With a fixed value of AVD at AVD1, a scan of the VVD is performed along the axis S1. The maximum VVD is found at VVD1. If from this local maximum VVD1, a scan of the AVD is performed along the axis S2, and a local maximum point is found at point P1.

If, however, the value of the VVD is fixed at VVD2 and that the AVD is scanned along axis S3, a local maximum AVD is found at AVD2. From this local maximum AVD2, a scan of the VVD is performed along axis S4, and another local maximum point is found at point P2.

Thus, the optimization of the VVD, then of the AVD, leads to an optimum at P1, while the optimization of the AVD and then the VVD leads to another optimum P2. These two points P1 and P2 are not only different from one the other, but also different from the real optimum located at P.

Therefore, an algorithm using two independent closed-loop systems, one for the AVD and the other for the VVD, would not always find the global optimum.

A preferred process in accordance with the present invention, as will be described below, comprises:
first, generation of an error signal to guide the digital PID controller to the optimal point $Z_{opt}$ and
second, use of the error signal thus generated to simultaneously perform closed-loop assessments of the AV and VV delays.

Generation of the Error Signal

The method for generating the error signal is described with reference to FIGS. 6 and 7. To determine the position of the current AVD and VVD values (i.e., values currently programmed into the device) compared to optimal values $AVD_{opt}$ and $VVD_{opt}$ that correspond to the global optimum $Z_{opt}$, the following steps are performed:
modulating the delays AVD and VVD, so that the delays vary in a deterministic and known manner around their current value(s), and
observing the changes resulting from the hemodynamic signal Z to derive an error signal and extracting information about the error signal by means of demodulation.

The modulation and demodulation apply separately to the AVD and VVD, or simultaneously on both. To ensure patient comfort, however, an independent modulation of the AVD and VVD is preferable. The choice of modulation and of the demodulation depends on the characteristics of the hemodynamic surface.

Figure 6:
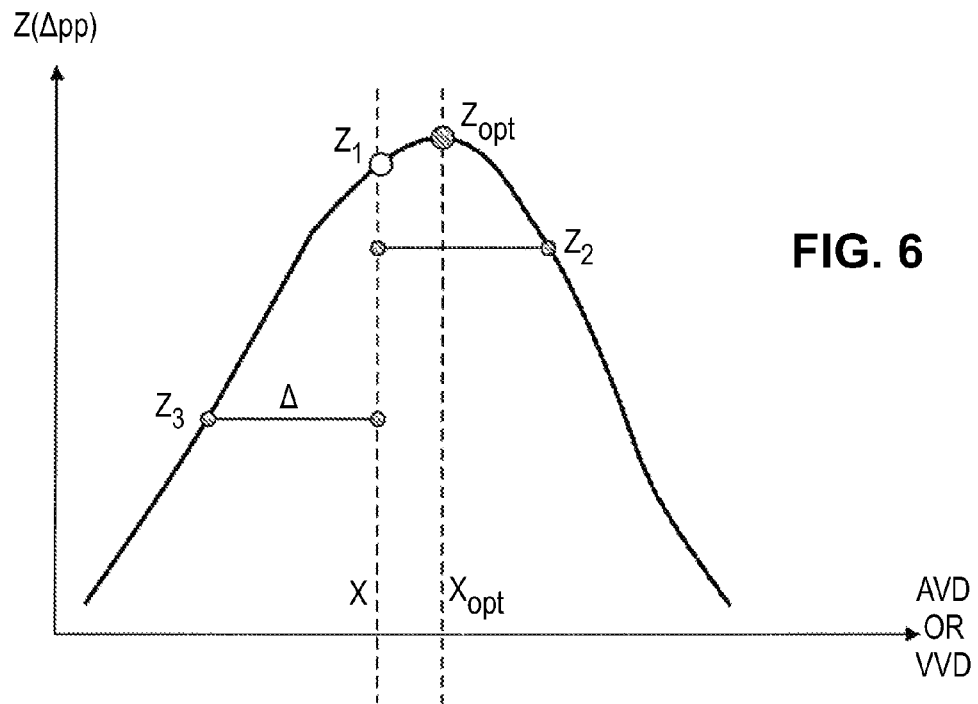
FIG. 6 shows a variation in the hemodynamic function according to the AVD or to the VVD, in the case of a sensor measuring the differences between the systolic and the diastolic pressures.

As shown in FIG. 6, in the case of a blood pressure sensor, the difference $\Delta pp$ between the systolic pressure and the diastolic pressure is illustrated as the hemodynamic parameter Z. Near the optimum $Z_{opt}$, the hemodynamic surface Z is approximately a parabolic surface, both for a variation of the AVD and for a variation of VVD. The current value of either the AVD delay or the VVD delay is noted as X.

It is assumed that the function $Z=H(X-X_{opt})$ is an even function around $X_{opt}$ that corresponds to the optimal delay value (either AVD or VVD). Specifically, any function with a similar maximum can be approximated by a symmetric quadratic function in a vicinity of $X_{opt}$ and, in any event, if the function is not perfectly symmetrical, the control algorithm converges to a limit $X'_{opt}$ close to $X_{opt}$, the difference having no significant impact on the final outcome from the clinical perspective for the patient.

The modulation of the delay X is performed by varying the delay X around its current value, with a modulation step of $\Delta$ milliseconds. The device is sequentially programmed with three different values of X (AVD or VVD):
X, the current value of the AVD (or VVD), which generates a hemodynamic value $Z_1=H(X-X_{opt})$;
X+$\Delta$, which generates a hemodynamic value $Z_2=H(X+\Delta-X_{opt})$; and
X−$\Delta$, which generates a hemodynamic value $Z_3=H(X-\Delta-X_{opt})$.
According to one embodiment, the demodulation is performed by multiplying the measured signal by +1 or −1, depending on the direction of the modulation. In other words, the samples $Z_2$ and $Z_3$ are passed in a first-order differentiator filter with two coefficients, +1 and −1, i.e., $Z_2$ is multiplied by +1 and $Z_3$ by −1. The error signal obtained at the demodulator output is thus $E=Z_2-Z_3$.

In the case of an even function H, the error signal E can be written as $E=2p(X_{opt}-X)$, $p=-H'(\Delta)=H'(-\Delta)$, p being the slope of the hemodynamic curve at $X=X_{opt}-\Delta$ (or $X=X_{opt}+\Delta$). Thus, the error signal obtained after modulation and demodulation is proportional to the difference between the target delay $X_{opt}$ and the current delay X. The sensitivity of the error signal depends on the slope p of the hemodynamic curve Z. The slope of this curve is equal to zero when $X=X_{opt}$. When the modulation step $\Delta$ is small, the slope p is also small. The selection of the size of the step $\Delta$ depends on the quality of the hemodynamic signal.

When the hemodynamic function is almost flat, the slope p is small, and the error signal E is not very sensitive to variations in X. This scenario can be detected by estimating the curvature of the hemodynamic surface using the measure $Z_1$. The curvature C is estimated by: $C=2Z_1-Z_2-Z_3$. When the curvature C is smaller (in absolute value) than a predefined threshold, it is preferable not to use the error signal E. In this case, the delay X is not adjusted (neither modulated nor demodulated), and the current delay X is used as the optimal delay $X_{opt}$.

Some CRT devices allow programming of the delays with only a limited number of predefined values. With limited choices of modulation steps $\Delta$, the modulation may not be symmetrical around the current delay X. For the modulation step $\Delta_2$ associated with the measurement $Z_2$ and the modulation step $\Delta\Delta_3$ associated with the measurement $Z_3$, the error signal E' is obtained by:

$$E' = 2\frac{(\Delta_2 - \Delta_3)Z_1 + \Delta_3 Z_2 - \Delta_2 Z_3}{(\Delta_2 + \Delta_3)}.$$

The error signal E' is zero when X coincides with $X_{opt}$.

Figure 7:
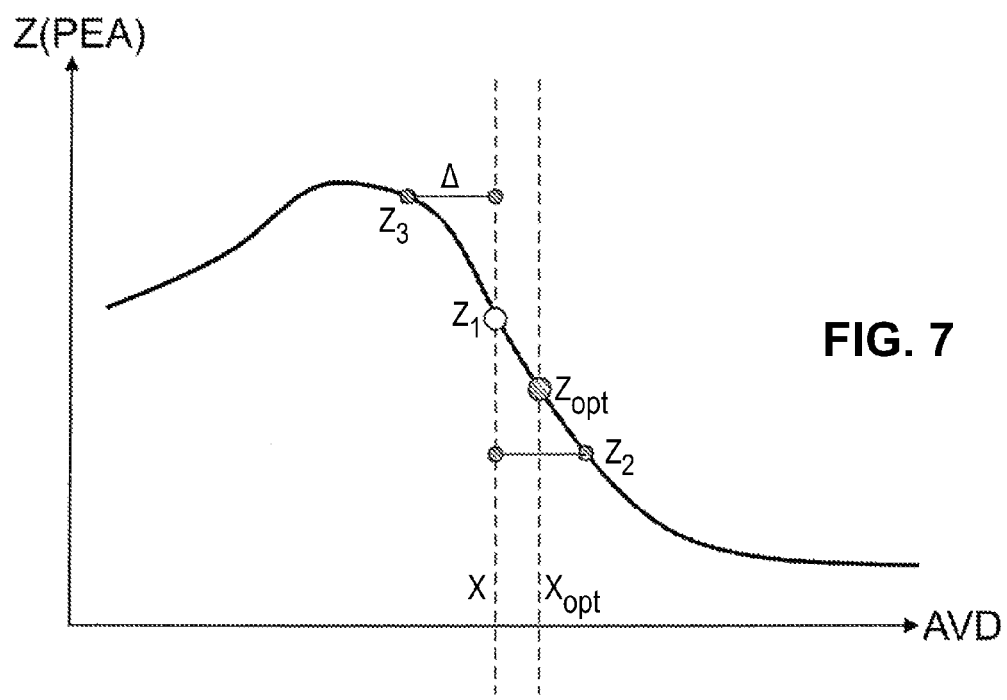
FIG. 7 illustrates a variation in the hemodynamic function according to the AVD, in the case of a sensor measuring the value of the peak of endocardial acceleration (PEA)

As shown in FIG. 7, in case of an endocardial acceleration sensor, the hemodynamic parameter Z corresponds to the amplitude of PEA based on the variation of the AVD. The hemodynamic parameter Z is of a sigmoid shape, and the optimum $Z_{opt}$ does not correspond to an extremum (as in the case of FIG. 6) but rather to a point of inflection of the sigmoid.

In this case, the method for generating the error signal is modified as follows. It is assumed that near the optimum $Z_{opt}$, the function Z can be expressed as $Z=Z_{opt}+G(X-X_{opt})$, G being an odd function around $X_{opt}$ and X being the current value of the AVD.

In general, a function with an inflection point can be approximated by an odd function G in a vicinity of the inflection point, in this case $X_{opt}$. If the function G is not completely odd, the control algorithm converges to a delay $X'_{opt}$ close to $X_{opt}$, and the difference have no significant impact on the final outcome from the clinical perspective for the patient.

The modulation is performed by varying X around its current value with a modulation step of $\Delta$ milliseconds. The device is sequentially programmed with three different values of AVD:
X, the current value of the AVD, which generates an hemodynamic value $Z_1=Z_{opt}+G(X-X_{opt})$;
X+$\Delta$, which generates an hemodynamic value $Z_2=Z_{opt}+G(X+\Delta-X_{opt})$ X−Δ, which generates an hemodynamic value $Z_3=Z_{opt}+G(X-\Delta-X_{opt})$.

The demodulation is performed by passing the samples $Z_3$, $Z_1$ and $Z_2$ in a second-order differentiator filter with three coefficients, respectively −1, +2 and −1. In other words, $Z_1$ is multiplied by 2, $Z_2$ is multiplied by −1 and $Z_3$ is multiplied by −1.

In this case, the error signal obtained at the output of the demodulator is written as: $E=2Z_1-Z_2-Z_3$. This error signal can be rewritten as: $E=2(p_0-p_1)(X_{opt}-X)$, where the values $p_0$ and $p_1$ are those of the (positive) slopes $p_1=-G'(\Delta)$ and $p_0=-G'(0)$.

Thus, the error signal obtained after modulation and demodulation is proportional to the difference between the target delay $X_{opt}$ and the delay to be controlled X.

When the hemodynamic value Z linearly varies with X, any point X gives a zero error signal because the second derivative (which defines the inflection point) is zero everywhere when $p_0=p_1$.

The sensitivity of the error signal in the case of seeking an inflection point thus depends on the difference $p_0-p_1$. Therefore, it is better to choose a modulation step Δ large enough to maximize this sensitivity. When the hemodynamic function is almost flat or linear, the difference $p_0--p_1$ is small, and the error signal E is insensitive to variations in X. In this case, it is preferable not to use the error signal E. In this case, the delay X is not adjusted (neither modulated nor demodulated), and the current delay X is used as the optimal delay $X_{opt}$.

Some CRT devices allow programming of the delays (AVD or VVD) with a limited number of predefined values. With the limited choice of modulation steps Δ, the modulation may not be perfectly symmetrical around the current delay X. If $\Delta_2$ is the modulation step associated with the measurement $Z_2$ and $\Delta_3$ the modulation step associated with the measurement $Z_3$, the error signal is obtained by:

$$E' = 2\frac{(\Delta_2 + \Delta_3)Z_1 - \Delta_3 Z_2 - \Delta_2 Z_3}{(\Delta_2 + \Delta_3)}.$$

The error signal E' is equal to zero when X coincides with $X_{opt}$.

The sequence of modulation/demodulation during a cardiac cycle is operated as follows (either for the AVD or the VVD):

a) measuring hemodynamic signal $Z_1$ for a value X of the AVD or the VVD,
b) modifying the delay: $X=X+\Delta$,
c) measuring the resulting hemodynamic signal $Z_2$,
d) modifying the delay: $X=X-\Delta$,
e) measuring the resulting hemodynamic signal $Z_3$,
f) calculating the error signal $E=Z_2-Z_3$ (or $E=2E_1-Z_2-Z_3$, as appropriate).

In one embodiment, the signals $Z_1$, $Z_2$ and $Z_3$ at steps a), c) and e) are measured either over one cardiac cycle, or by taking an average over several cardiac cycles depending on the response time of the measured parameter to the changes in the AVD or VVD. For some hemodynamic sensors, it may be necessary to wait for one or more cardiac cycles so that the hemodynamic response is stabilized after modifying the delay in steps b) and d)).

Simultaneous Closed-Loop of the AVD and of the VVD from the Error Signal

Figure 8:
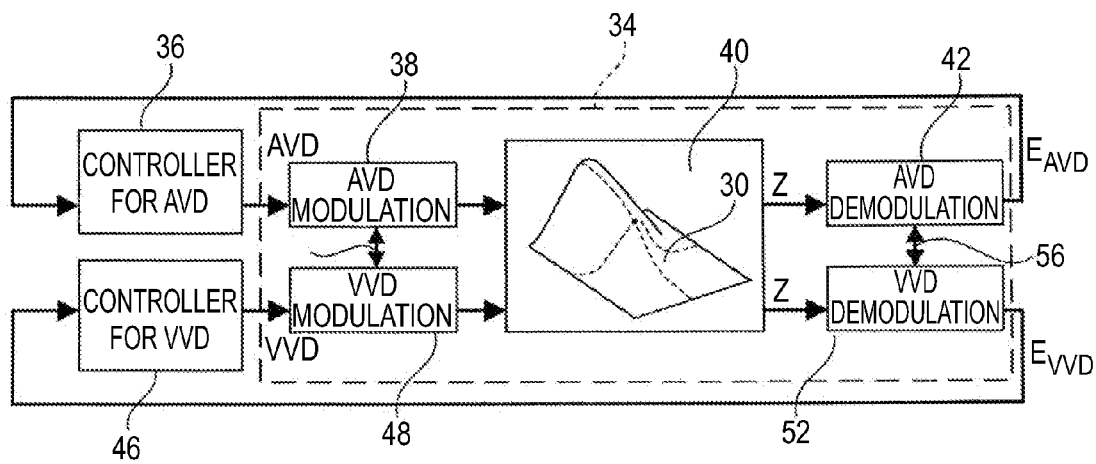
FIG. 8 shows a flow chart to obtain an optimization of the hemodynamic parameters using two interdependent PID loops with modulation/demodulation of the AVD and of the VVD.
Figure 9:
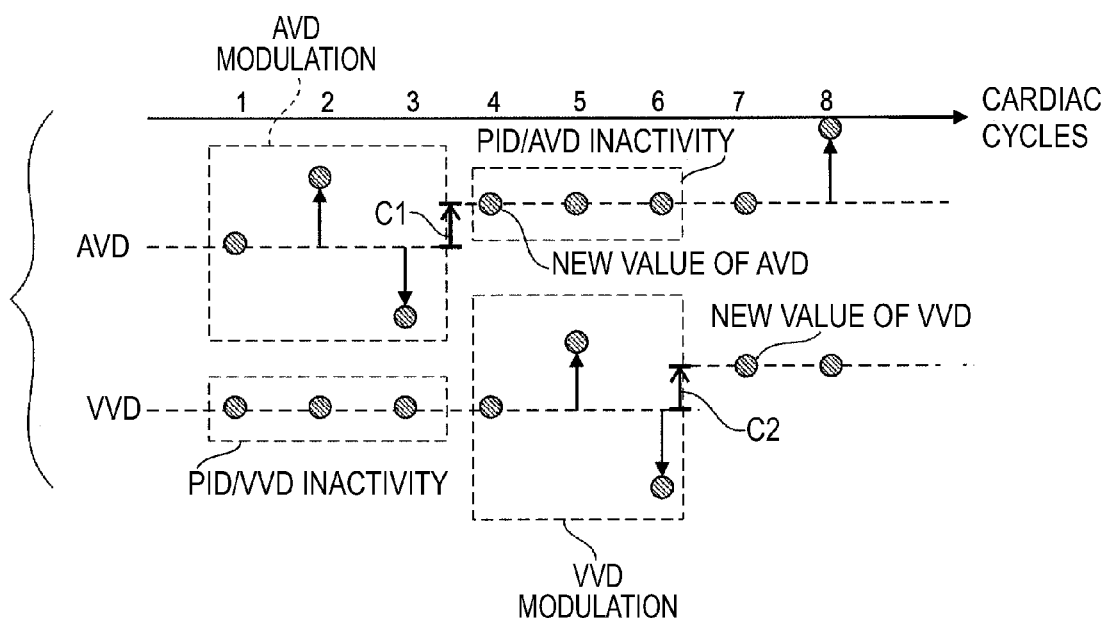
FIG. 9 is a timing diagram showing how the AVD and VVD parameters change during a search for an optimum, over successive cardiac cycles.
Figure 10:
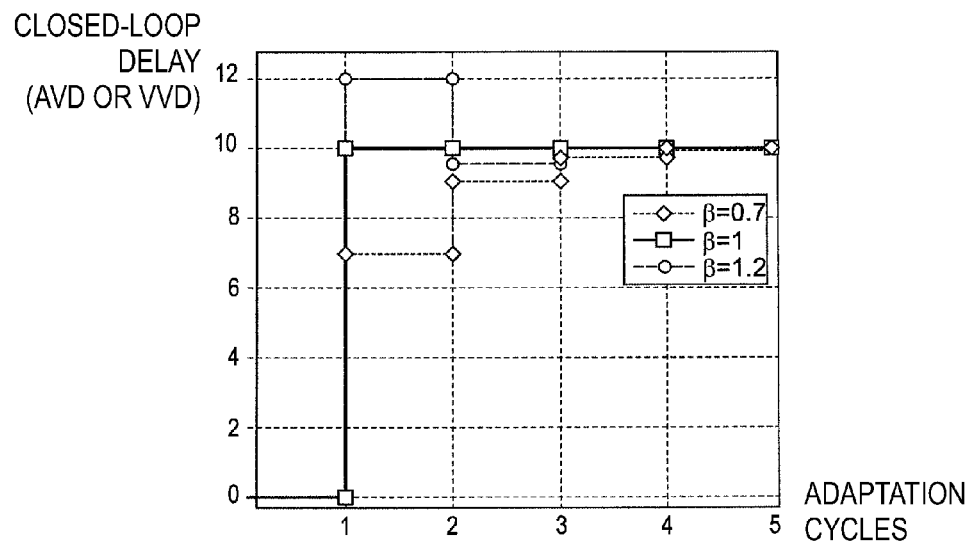
FIG. 10 illustrates a response of the closed-loop PID at each adaptation step, for various gain settings of the loop.
Figure 11A:
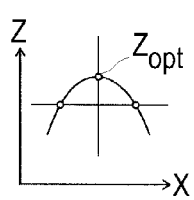
FIG. 11 illustrates different possible characteristics of the sensor signal as a function of the delay (AVD or VVD), to obtain an error signal for controlling the closed-loop.
Figure 11B:
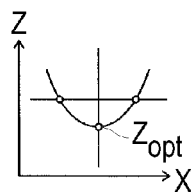
Figure 11C:
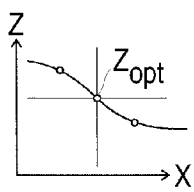
Figure 11D:
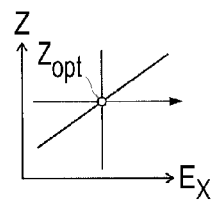

With reference to FIGS. 8-10, a preferred algorithm in accordance with the present invention for using the AVD and VVD error signals generated by the by the modulation/demodulation described above, will now be described.

In one embodiment, the classical theory of closed-loop control systems is used to realize a simple digital controller to monitor the optimal AVD and VVD.

As shown in FIG. 8, the system includes two closed-loop systems for each of the two delays AVD and VVD. Each of these closed-loops includes a respective dedicated controller 36, 46, including a PID controller (e.g., a non-restrictive type) associated with the error generation block 34.

The closed-loop of the AVD includes a PID controller 36 receiving as input an error signal $E_z$ related to the AVD and delivering as output a control signal applied to a modulator circuit 38 for, as explained above with reference to FIG. 6, modulating in a controlled manner the value of AVD around the optimal value to be sought.

Block 40 represents the system responsive to a variation of the AVD. The overall system includes (see FIG. 1) the CRT generator 10, the patient's heart, the hemodynamic sensor 18, and the acquisition circuit 20. This block 40 incorporating the function represented by the hemodynamic surface 30 generates hemodynamic signal Z. The hemodynamic signal Z is demodulated by block 42, and the error signal $E_z$ is delivered as an input to the PID controller 36.

Similarly, the closed-loop of the VVD includes a PID controller 46 receiving as input an error signal $E_z$ related to the VVD and delivering as output a signal of control of the VVD applied to a modulator circuit 48 for, as explained above with reference to FIGS. 6 and 7, modulating in a controlled manner the value of the VVD around the optimal value to be sought. The block 40 provides hemodynamic signal Z. The hemodynamic signal is demodulated by the block 52, and the error signal $E_z$ is delivered as an input to the PID controller 46.

As explained above with reference to FIG. 5, an independent research of the optima for the AVD and the VVD generally leads to local optima that are different from the global optimum to be sought.

The two interdependent closed-loops interact between the blocks of modulation and of demodulation of the AVD and VVD, as shown by arrows 54 and 56. The interaction may in particular result from a specific sequence of the cycles of modulation/demodulation of the AVD and the VVD, respectively.

An example of a specific sequence is shown in FIG. 9. As noted above with respect to the generation of the error signal, the error signal E is available after demodulating the values $Z_1$, $Z_2$ and $Z_3$ that correspond to the successive respective values X, X+Δ and X−Δ of the delay X (AVD or VVD). Therefore, at least three cardiac cycles are required to obtain an error signal for each of the AVD or VVD delays.

The PID controller 36 (or 46) sequentially operates an update of the delay after multiplication of this error signal by a gain, and then integration. For the AVD, the corresponding PID controller 36 waits for three cardiac cycles to receive an error signal. It then performs an update of the AVD controlled at its output, and remains idle for the following three cardiac cycles, during which the PID controller 46 for the VVD takes over, and so on, alternating the operation of the two PID controllers 36 and 46 ensuring the convergence and the simultaneous monitoring of both optimal delays, $AVD_{opt}$ and $VVD_{opt}$.

In FIG. 9, the values of the AVD and VVD delays during a sequence of eight cardiac cycles, are illustrated. During cycles #1 to #3, the AVD is modulated and the VVD is maintained at its current value (inhibition of modulation of the VVD). At the end of cycle #3, an error signal C1 is calculated for the AVD. This signal C1 is applied at the input of the PID controller 36 dedicated to the AVD, and a new value of the AVD is so determined as an output of the controller 36.

The VVD is then modulated during the cycles #4 to #6, keeping unchanged the value of the AVD just obtained (that is to say that the modulation of the AVD is inhibited during these three cycles). At the end of cycle #6, an error signal C2 of the VVD is calculated and applied to the PID controller 46 dedicated to the VVD, providing as output a new value of the VVD applied to the device (Cycle #7). In cycle #8, the described process is repeated by applying an AVD modulation, and so on. The cycles #7, #8 and #9 correspond to the cycles #1, #2 and #3 of the succeeding iteration. A complete cycle of adapting the system to the new values of the pair AVD/VVD therefore requires at least six cardiac cycles.

The condition for stability and convergence of the dual closed-loop system as described above is evaluated as follows. Let k be the time index for a PID controller (the controller 36 for the AVD or the controller 46 for the VVD). A cycle of adaptation of the closed-loop system corresponds to the passage from k to k+1 that is a duration of at least six cardiac cycles.

The error signal provided to the PID controller is written:

$$E_k = s(X_{opt} - X_k),$$

where s is the sensitivity of each controller that depends on the modulation step $\Delta$ and the shape of the hemodynamic function.

The PID controller corrects $X_k$ according to the equation:

$$X_{k+1} = X_k + gE_k,$$

where g is the gain of the loop.

The z transform of the transfer function K between the current controlled delay X and the optimum delay $X_{opt}$ is expressed as:

$$\frac{X}{X_{opt}} = K(z) = \frac{\beta}{z - 1 + \beta}$$

in which $\beta = g.s$.

The behavior of the closed-loop in the long term is determined by the limit of this function when z tends to 1. As lim K (z)=1 and as the loop is closed, the controlled delay X converges to $X_{opt}$ provided that the stability condition of the closed-loop is verified. This condition can be expressed as:

$$0 < \beta < 2 \Leftrightarrow 0 < g < 2/s$$

The loop gain thus depends on the sensitivity s of the controller.

FIG. 10 shows the evolution of the controlled delay X in response to a step in $X_{opt}$ of 10 ms for three values of $\beta$: for $\beta=1$, the controlled delay X coincides with the optimum time after a single cycle of adaptation, while for $\beta<1$ the system monotonically converges and for $\beta>1$ the controlled delay hovers around $X_{opt}$.

In practice, the value of the sensitivity s is not known. It can be estimated for a given patient and a given sensor, at least once, for example, at the time of implantation of the sensor. In any event, it is nevertheless preferable to choose a gain smaller than 1/s, to avoid oscillations and allow a margin of stability if the sensitivity s increases over time.

In another embodiment, stability is ensured by applying a closed-loop algorithm of the "PID truncated" type with limited adjustments to a given maximum value $c_k = \min(20, \max(-20, gE_k)$, for example, limiting adjustments to ±20 ms.

A closed-loop algorithm of the "PID truncated" type is applied to the case of an hemodynamic signal delivered by the PEA sensor in the following steps:
  a) Perform a complete scan when the sensor is installed
  b) Estimate the slope p for the VV curve, $p_0$, and $p_1$ for the AV curve, the minimum slope $P_{threshold}$ for AV and the minimum curvature $C_r$ threshold for VV
  c) Select the gain $g_1 = 0.35/p$ for the VV loop
  d) Select the gain $g_2 = 0.35/(p_0 - p_1)$ for the AV loop
  e) $AV_p = 120$ ms, $VV_p = 0$ ms, $\Delta_1 = 10$ ms, $\Delta_2 = 15$ ms
  f) Program $AV = AV_p$ and $VV = VV_p$
  g) Start the servo loop:
    1. Measure $Z_1$
    2. Program $AV = AV_p + \Delta_2$
    3. Measure $Z_2$
    4. Program $AV = AV_p - \Delta_2$
    5. Measure $Z_3$
    6. $E = g2*(2*Z_1 - Z_2 - Z_3)$
    7. $P = Z_3 - Z_2$
    8. $C = \min(20, \max(-20, E))$
    9. If $P > P_{threshold}$
    10. Program $AV = AV_p$ In an alternative implementation of the algorithm, a control algorithm of the "PID sign" type, with a fixed step, of 5 ms, for example, is applied. In this case, each PID controller performs an update according to the relationship $X_{k+1} = X_k + 5*\text{sign}(E_k)$, in which sign ( . . . ) represents the sign function (equal to 1 if $E_k$ is positive and to −1 otherwise). Stages 6-9 of the above algorithm, then come to:
  1. $E = 2*Z_1 - Z_2 - Z_3$
  2. $AV_p = AV_p + \text{sign}(E)*5$ This variant is advantageously robust, however has a disadvantage of perpetually oscillating around the optimum time.

Variants of Implementation of the Invention

The implementation of the present invention is not limited to cases where the error signal is obtained by a technique of modulation/demodulation. Specifically, FIG. 11 illustrates several types of signal Z delivered by the hemodynamic sensor 18 depending on the variation of the X delay (AVD or VVD). FIG. 11 (*a*) corresponds to the case illustrated in FIG. 6, in which the optimum $Z_{opt}$ is located at the curve (supposed to be a pair at this point) maximum, and the optimum is possibly reached by successive approximations using the technique of modulation/demodulation as described above. This characteristic curve is obtained from the difference $\Delta_{pp}$ between the systolic pressure and the diastolic pressure that are measured by a blood pressure sensor.

FIG. 11 (*b*) corresponds to a characteristic of the same type, in which a minimum of the curve is sought. The minimum is supposed to be pair in the vicinity of the optimum $Z_{opt}$. This characteristic curve is typically obtained by measuring the width of the QRS complex on the ECG. It may be referred in particular to David Tamborero and al., *Optimization Of The Delay in Cardiac Resynchronization interventricular Therapy Using The QRS Width*, American Journal of Cardiology, 15 Nov. 2009, Vol. 104, Issue 10, pp. 1407-1412, which describes an optimization process in which the optimum VVD delay corresponds to the narrower QRS complex.

FIG. 11 (*c*) corresponds to the case illustrated in FIG. 7, with a characteristic of the sigmoid type, which is typical for a signal delivered by an endocardial acceleration sensor, such as a sensor giving the value of the PEA peak based on the AVD. In this case, the optimum $Z_{opt}$ is at the inflection point of the curve, assumed to be odd near the inflection point, and the error signal is generated by a technique of modulation/demodulation as described above.

In the case of FIG. 11 (d), however, the sensor delivers a signal directly proportional to the error signal, in which the optimum $Z_{opt}$ is located at the origin, and the signal $Z=k*E_x$ is substantially proportional to the sought error signal $E_x$. It is not necessary in this case to operate by modulation/demodulation, insofar as the error signal is directly readable at the output of the sensor. This characteristic curve is obtained, for example, from a sensor of the "zero crossing" type such as a differential bio-impedance sensor delivering a signal depending on the phase difference between the bioimpedance measured in the left ventricle (LVZ) and the one measured in the right ventricle (RVZ). U.S. 2008/0114410 describes, among other things, a system for optimizing the AV delay of a CRT device by measuring the differential bioimpedance.

Figure 12:
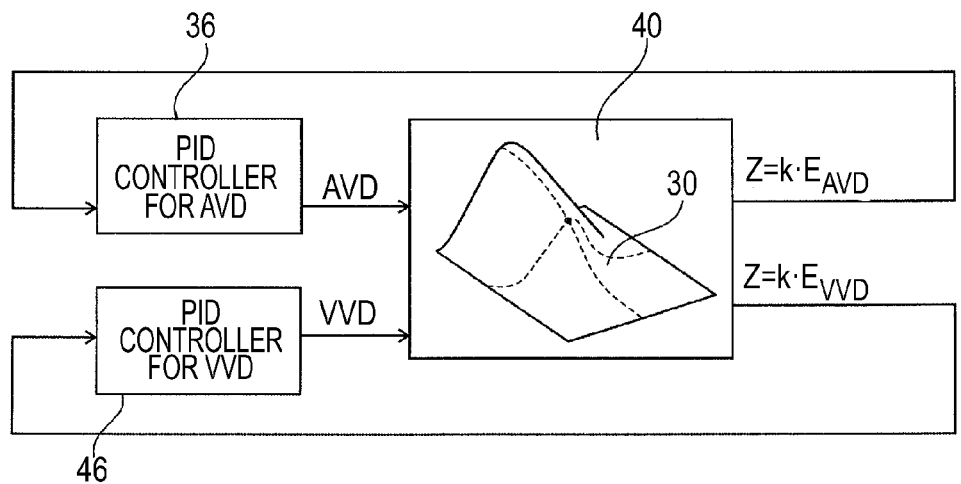
FIG. 12 shows a flow chart to obtain an optimization of the hemodynamic parameter using two PID loops directly controlled by a sensor to obtain a direct measure of the error.

FIG. 12 is a counterpart of FIG. 2, in a scenario in which both of the error signals $E_{AVD}$ and $E_{VVD}$ of the AVD and the VVD, respectively, can be obtained directly from the signal Z delivered by the hemodynamic sensor 18. In this case, the signal Z is applied to the input of the PID controller 36 for controlling the AVD, and in the same manner, to the input of PID controller 46 for controlling the VVD.

Figure 13:
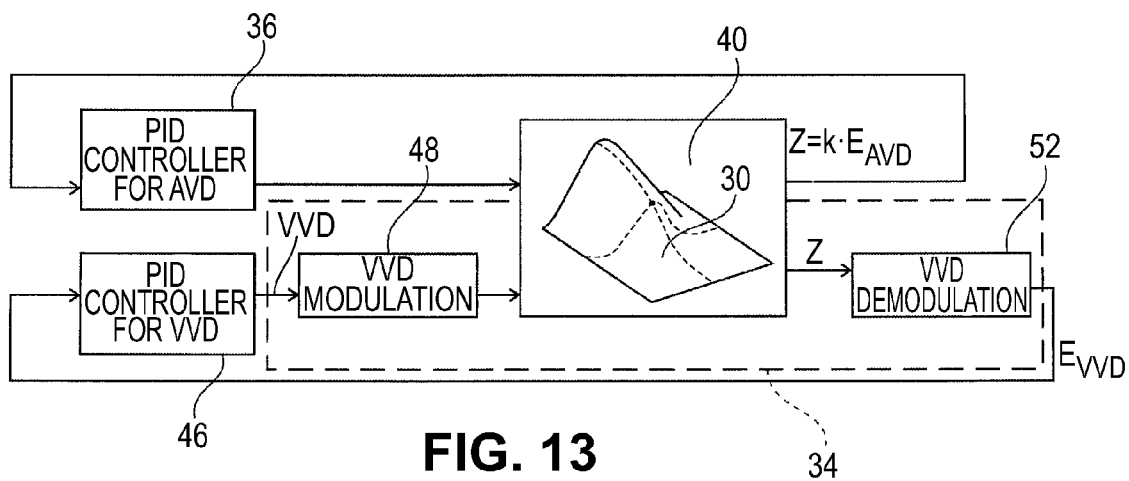
FIG. 13 shows a flow chart to obtain an optimization of the hemodynamic parameter using two PID loops, one of which is controlled by a sensor to directly obtain the error signal.

FIG. 13 illustrates an intermediate case in which the error signal of one of the delays, for example, the error signal $E_{AVD}$ of the VVD, is directly obtained from the signal Z delivered by the hemodynamic sensor 18, while the signal error $E_{VVD}$ of the VVD to be applied to the input of the PID controller 46 for control of the VVD requires a modulation/demodulation of the VVD.

In both cases of FIGS. 12 and 13, it is necessary to have two separate PID controllers for both AVD and VVD delays. However, insofar as it is possible to directly obtain an error signal for at least one of the delays, there is no need to alternate periods of modulation/demodulation on each of two loops, as it had been described with reference to FIGS. 9 and 10, with alternating periods of inactivity of one of the PID controllers while generating the error signal for the other loop.

One skilled in the art will appreciate that the present invention may be practiced by other than the embodiments described above, which are presented for purposes of illustration and not of limitation.

The invention claimed is:

1. An active implantable medical device for resynchronization by biventricular pacing, comprising:
    means for detecting atrial and ventricular events;
    means for stimulating right and left ventricles;
    at least one sensor (18) delivering a hemodynamic signal (Z) representative of a patient's current hemodynamic parameter;
    means for applying to the means for stimulating an atrio-ventricular delay AVD, the AVD being counted from the detection of a spontaneous or paced atrial event until a pacing of the right ventricle is applied in the absence of a sensed spontaneous ventricular event;
    means for applying to the means for stimulating an inter-ventricular delay VVD between the respective moments of stimulation of the right and left ventricles; and
    closed-loop means (22), for continuously monitoring the AVD and the VVD according to the hemodynamic signal delivered by the at least one sensor,
    means for generating an error signal of AVD (34) according to the hemodynamic signal delivered by said at least one sensor (18), the error signal of AVD ($E_{AVD}$) being representative of a difference between the AVD and an optimum value of the AVD ($AVD_{opt}$), the means for generating an error signal of AVD comprising means for modulating (38) and demodulating (42) the AVD;
    means for generating an error signal of VVD (34) according to the hemodynamic signal delivered by said at least one sensor (18), the error signal of VVD ($E_{VVD}$) representative of a difference between a current value of the VVD and an optimum value of VVD ($VVD_{opt}$), the means for generating an error signal of VVD comprises means for modulating (48) and demodulating (52) the VVD being functionally interdependent with the means for modulating (38) and demodulating (42) the AVD;
    a closed-loop regulator (36) for controlling the AVD, receiving as input said error signal of AVD ($E_{AVD}$) and outputting a signal of AVD; and
    a closed-loop regulator (46) for controlling the VVD, receiving as input said error signal of VVD ($E_{VVD}$) and outputting a signal of VVD.

2. The device of claim 1, wherein said closed-loop regulators (36, 46) for controlling the AVD and the VVD further are PID regulators.

3. The device of claim 1, wherein either of said means for modulating (38, 48) and demodulating (42, 52) the VVD and the AVD or the regulators (36, 46) for controlling the AVD and of the VVD further comprise means for controlling alternately the modulating and demodulating the AVD and the VVD over a predetermined number of cardiac cycles, and wherein the regulator for control of the AVD is inoperative during the modulation/demodulation of the VVD, and vice versa.

* * * * *